(12) United States Patent
Suetsuna et al.

(10) Patent No.: US 6,217,879 B1
(45) Date of Patent: Apr. 17, 2001

(54) ENZYME-DECOMPOSED MATERIALS OF LAVER AND USES THEREOF

(75) Inventors: Kunio Suetsuna, Yamaguchi-ken; Masanobu Saito, Chiba-ken, both of (JP)

(73) Assignee: Shirako Co., Ltd., Tokyo (JP)

( * ) Notice: Subject to any disclaimer, the term of this patent is extended or adjusted under 35 U.S.C. 154(b) by 0 days.

(21) Appl. No.: 09/397,014

(22) Filed: Sep. 15, 1999

(30) Foreign Application Priority Data

Sep. 25, 1998 (JP) .................................................. 10-270906
Aug. 10, 1999 (JP) .................................................. 11-226165

(51) Int. Cl.⁷ .......................... A61K 35/78; A61K 38/00; A01N 37/18
(52) U.S. Cl. ............................................. 424/195.1; 514/2
(58) Field of Search .............................. 424/195.1; 514/2, 514/17–19

(56) References Cited

U.S. PATENT DOCUMENTS 4,981,699 * 1/1991 Inada et al. ............................... 426/7

FOREIGN PATENT DOCUMENTS

2282566 * 12/1987 (JP) .
5015388 * 1/1993 (JP) .
10-175997 6/1998 (JP) .

OTHER PUBLICATIONS

Kunio Suetsuna, "Purification and Identification of Angiotensin I–Converting Enzyme Inhibitors From the Red Alga *Porphyra Yezoensis*," Journal of Marine Biotechnology, (1998), 6:163–167.

* cited by examiner

*Primary Examiner*—Christopher R. Tate
(74) *Attorney, Agent, or Firm*—Oblon, Spivak, McClelland, Maier & Neustadt, P.C.

(57) ABSTRACT

The present invention provides materials from laver (a seaweed) as the starting material, which are useful in the field of pharmaceutical preparation, the field of health food, etc. The present invention relates to enzyme-decomposed materials from laver comprising a peptide mixture having an antihypertensive action obtained by decomposing laver with pepsin, wherein laver is boiled as a starting material for 1 hour or more and then the broth is removed whereby their antihypertensive action is further raised while their bitter taste, smell, viscosity etc. are eliminated. Accordingly, these enzyme-decomposed materials are made further useful as an antihypertensive agent and also suitable when added to food for use as health food. Further, these materials after decomposed with pepsin are further decomposed with an enzyme having a peptidase activity thereby improving tastes and providing more suitable food additives.

20 Claims, 4 Drawing Sheets

ENZYME-DECOMPOSED MATERIALS OF LAVER AND USES THEREOF

BACKGROUND OF THE INVENTION

1. Field of the Invention

The present invention relates to novel enzyme-decomposed materials from laver (a seaweed) which have a wide variety of effective pharmacological actions, as well as uses thereof.

2. Discussion of the Background

Heretofore, laver has been used exclusively as food, but the present inventors have focused their attention on the functions and components of laver and extensively studied decomposed materials from laver to utilize them in other fields. For example, the present inventors have decomposed laver with pepsin to obtain a peptide mixture as a substance having a wide variety of effective functions including antihypertensive action, and previously filed this substance for a patent (JP-A 10-175997).

The peptide mixture described above can be used in a pharmaceutical preparation as an antihypertensive agent or in health food having an inhibitory action on calcium precipitation, an anti-mutagenic activity, a plasma and hepatic cholesterol-reducing action, an effect of reducing blood sugar levels, an effect of improving hepatic functions, an anti-oxidant effect and a SOD-like activity, but the enzyme-decomposed product when used as a pharmaceutical preparation should further be purified to increase its action. Further, when it is used as food that does not require such high biological activity as in a pharmaceutical preparation, polysaccharides remain in the enzyme-decomposed material to make it highly viscous when dissolved in an aqueous solvent, so there is the problem that unless it is purified to certain degrees, its use is limited. Further, the enzyme-decomposed material tastes bitter or unfavorable smells, thus making its use limited.

The object of the present invention is to provide enzyme-decomposed materials from laver which are improved so as to be further readily usable in a wide variety of uses such as pharmaceutical preparation, food etc., thus solving the problems described above.

SUMMARY OF THE INVENTION

That is, the present invention relates to enzyme-decomposed materials (A) from laver, comprising a peptide mixture obtained by boiling laver as the starting material for 1 hour or more, then removing the broth and adding water and pepsin to decompose the laver with pepsin, as well as to enzyme-decomposed materials (B) from laver, comprising a peptide mixture obtained by decomposing laver with pepsin in the method described above and further decomposing it with an enzyme having a peptidase activity.

Further, the present invention relates to use of enzyme-decomposed materials (A) and (B) from laver, to an antihypertensive agent comprising these enzyme-decomposed materials, and to health food and low salt food comprising these enzyme-decomposed materials added to food. Further, the present invention relates to a seasoning comprising the latter, that is, the enzyme-decomposed materials (B) as a major ingredient.

For production of the enzyme-decomposed materials from laver according to the present invention, the starting material laver is boiled for 1 hour or more, and before enzyme decomposition, its broth is removed so that components other than proteins that are the starting material of peptides are removed, thereby raising the degree of enzyme decomposition and promoting formation of peptides having an antihypertensive action, an inhibitory action on calcium precipitation, an antimutagenic activity against mutagens, a plasma cholesterol-reducing action, a cerebral apoplexy preventing effect, hepatic cholesterol-reducing action, an effect of improving hepatic functions, a SOD-like activity, an anti-oxidant effect and an effect of reducing blood sugar levels.

In the above-mentioned prior art invention, the boiling treatment and broth-removing treatment described above are not conducted before enzyme decomposition, and thus components other than desired peptides are contained in large amounts in the enzyme-decomposed materials, or the degree of enzyme decomposition itself is low, and as a result, it cannot be said that the antihypertensive action is satisfactory.

Because the boiling treatment and broth-removing treatment are conducted in the present invention, the inhibitory action of the product on angiotensin I converting enzyme, which is an indication of the ability to reduce blood pressure, was confirmed to be raised to 3- to 5-fold or more. The boiling treatment should be conducted using hot water from the start whereby water-soluble proteins in laver as the starting material are instantaneously heated and coagulated thereby preventing the proteins from being eluted into the broth.

As described above, the enzyme-decomposed materials from laver according to the present invention have a high inhibitory activity on angiotensin I converting enzyme, and even in a non-purified form, have an equivalent antihypertensive action to that of purified materials from said peptide mixture from laver in the above-mentioned prior art invention, so these can be easily applied to pharmaceutical preparations requiring high activity. For the field of food, unpleasant smell peculiar to laver can be removed by boiling treatment and subsequent broth-removing treatment, so the product can be added to food without any adverse effect on the flavor of the food. Accordingly, it can impart various functions without adversely affecting the flavor of the food, to provide more preferable health food.

Further, after the pepsin decomposition described above, secondary decomposition reaction with an enzyme having a peptidase activity is conducted so that free amino acid levels can be raised to 10% or more, whereby enzyme-decomposed materials from laver given tastes while maintaining an antihypertensive action can be obtained. Accordingly, the secondary decomposition reaction with an enzyme having a peptidase activity is preferably conducted if it is necessary to prepare enzyme-decomposed materials with good tastes where bitter tastes peculiar to proteins have been reduced. The enzyme having a peptidase activity used in secondary decomposition is preferably that having an activity for increasing free amino acid levels while keeping an inhibitory action on angiotensin I converting enzyme, and for example, mention can be made of Flavorzyme and Sumizyme.

By broth-removing treatment after boiling, the majority of impurities other than peptides have been removed from the enzyme-decomposed materials derived from laver according to the present invention, but other peptides and components other than active peptides are still present in very small amounts in the hydrolyzate. Accordingly, if the enzyme-decomposed materials of the present invention are purified for use, the materials with a higher antihypertensive action can be obtained. As a matter of course, the mixture after hydrolysis may be used as such in various uses. In the case of purification, ultrafiltration, absorbent treatment or other suitable techniques are adopted for removal of components other than peptides.

By a suitable means such as spray-drying and lyophilization, the enzyme-decomposed materials of the present invention may be dried alone or in combination with fillers such as starch and dextrin or with other food materials or food additives as necessary.

As described above, the enzyme-decomposed materials from laver according to the present invention exhibit an antihypertensive action, so these materials can be used as an antihypertensive agent. Further, the enzyme-decomposed materials from laver according to the present invention have an inhibitory action on calcium precipitation, an anti-mutagenic activity against mutagens such as Trp-P-1 and AF-2, a plasma and hepatic cholesterol-reducing action, a cerebral apoplexy preventing effect, an effect of improving hepatic functions, a SOD-like activity, an anti-oxidant effect and an effect of reducing blood sugar levels, so these materials can be added to food in order to form health food based on these actions.

Further, it was found that the enzyme-decomposed materials from laver according to the present invention have the effect of raising a salty taste, so these materials can be added to produce food of low salt type.

DETAILED DESCRIPTION OF THE PREFERRED EMBODIMENTS

Figure 1:
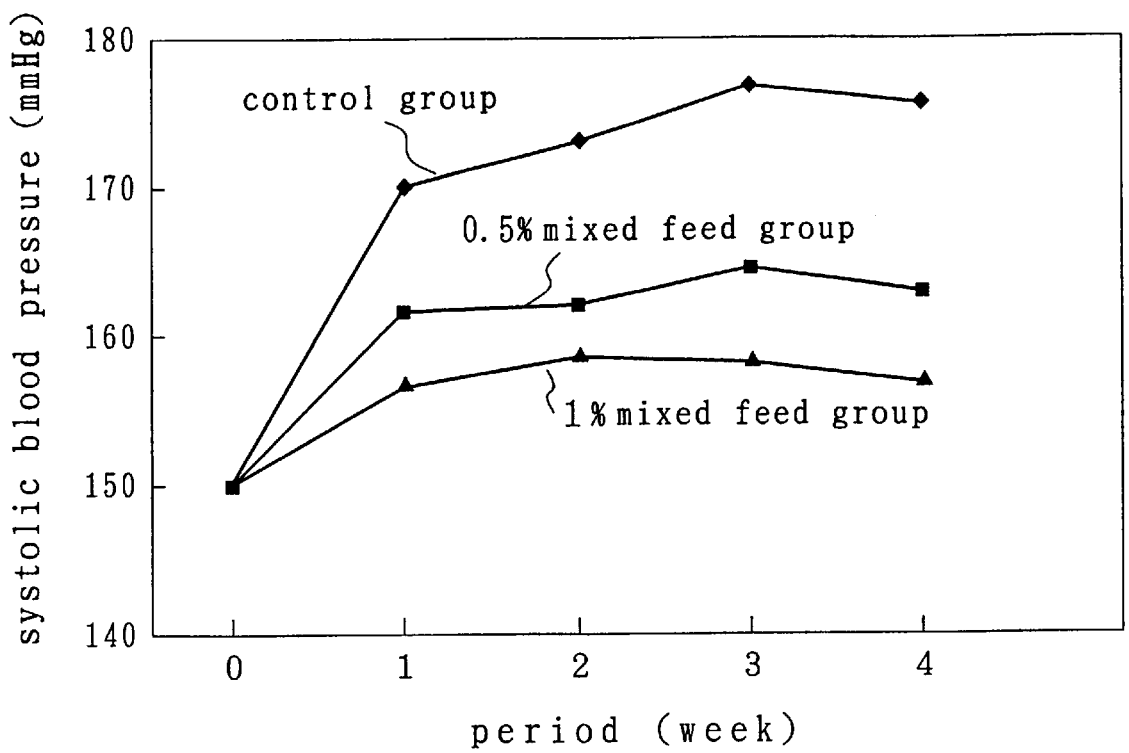
FIG. 1 is a diagram showing the result of a blood pressure measurement test by long-term administration of the enzyme-decomposed materials from laver according to the present invention into rats.

Hereinafter, the present invention is described in more detail with reference to the Examples.

EXAMPLE 1

(1) Preparation of Enzyme-decomposed Materials From Laver 50 kg of dry laver which had been finely divided to a size of 35 mesh in a high-speed grinder was added to 950 L of hot water previously heated at 95° C. and boiled for 1 hour, and the broth was removed. Then, 950 L water at 50° C. was added to the remaining laver and adjusted to pH 2.0 with HCl, and 2 kg of pepsin (Amano Pharmaceutical Co., Ltd.) was added thereto, and the mixture was reacted at 50° C. for 24 hours under stirring. The decomposed solution obtained by the reaction was adjusted to pH5.0 with 1 N NaOH and kept at 50° C. for 10 minutes to inactivate the pepsin, and the mixture was centrifuged at 14,000 rpm for 20 minutes, and the supernatant was filtered through a glass filter. Thereafter, after diatomaceous earth was added thereto as a filter aid, it was filtered again with a filter press, concentrated under reduced pressure, and immediately spray-dried whereby enzyme-decomposed materials of the dry laver were obtained.

In a comparative test, 2 kinds of enzyme-decomposed materials were obtained using the same starting material in the same manner as above except that the boiling treatment was not conducted, or that after the boiling treatment was conducted, the broth after the boiling treatment was not removed.

Concerning these 3 kinds of enzyme-decomposed materials, the viscosity of 10% aqueous solution was measured by a rotational viscometer and the absorbance of 0.2% aqueous solution was measured by a spectrophotometer, and their general ingredients were further analyzed, and these measurement results are shown in Table 1. The ratio (%) of the resulting enzyme-decomposed materials is also shown in Table 1.

TABLE 1

| Step | Dry laver → boiling treatment → broth removal → enzyme reaction | Dry laver → boiling treatment → enzyme reaction | Dry laver → enzyme reaction |
|---|---|---|---|
| Viscosity (mPa' sec) | 20 | 120 | 60 |
| absorbance (370 nm) | 0.45 | 0.75 | 0.77 |
| Yield (%) | 53.6 | 95.2 | 94.1 |
| Water content (%) | 2.5 | 2.9 | 2.8 |
| Protein (%) | 72.5 | 40.5 | 51.9 |
| Lipid (%) | 0.2 | 0.1 | 0.1 |
| Sugar (%) | 9.8 | 12.1 | 13.4 |
| Fiber (%) | 7.5 | 30.1 | 25.2 |
| Ash content (%) | 7.5 | 14.3 | 9.4 |

(2) Preparation of Enzyme-decomposed Materials By Secondary Enzyme Decomposition 1 kg of the enzyme-decomposed materials of laver obtained in item (1) above were dissolved in 50 L of water, then 10 g Flavorzyme® (Novo Nordisk A/S) was added thereto as the enzyme having a peptidase activity, and the materials were enzymatically decomposed at 50° C. for 6 hours and then kept at 80° C. for 10 minutes to inactivate the enzyme. Thereafter, diatomaceous earth and activated carbon were added thereto as filter aids and filtered off, and the filtrate was concentrated under reduced pressure and immediately spray-dried whereby enzyme-decomposed materials from laver were obtained.

The resulting enzyme-decomposed materials from laver, and the enzyme-decomposed materials from laver obtained in item (1) above, were examined for their free amino acid levels and simultaneously they were also examined in a 10-level sensory test by 10 examinees. The materials evaluated to be the best were rated at Point 10. The free amino acid levels and the average of the results in the sensory test are shown in Table 2.

TABLE 2

| Step | (A) Dry laver → boiling treatment → broth removal → enzyme reaction → secondary enzyme reaction | (B) Dry laver → boiling treatment → broth removal → enzyme reaction | (C) Dry laver → enzyme reaction |
|---|---|---|---|
| Ratio of free amino acids to total proteins (%) | 10.1 | 1.1 | 0.2 |
| Good taste | 9 | 5 | 5 |
| Sweetness | 10 | 5 | 4 |
| Salty taste | 5 | 5 | 6 |
| Flavor | 9 | 7 | 2 |

As shown in Table 2, the evaluated flavor is 2 for C, while it is 7 for B and 9 for A, so it is understood that the enzyme-decomposed materials from laver obtained in the process of the present invention indicate a reduced unpleasant smell peculiar to laver by boiling laver and then removing the broth.

Further, "A" subjected to secondary enzyme reaction indicates a high ratio of free amino acids and is rated high in tastes and sweetness in the sensory test.

(3) Purification of the Enzyme-decomposed Materials 0.5 kg of the enzyme-decomposed materials from laver obtained in item (1) above were dissolved in distilled water and applied to a Dowex-50 (H+) column ($\phi$20 cm×108 cm) substituted with HCl and washed with 20 L distilled water, and the adsorbed peptides were eluted with 2 N ammonia water. After the ammonia was removed from this eluate by an evaporator, it was lyophilized to give 360.7 g of the purified enzyme-decomposed materials of laver with a protein content of 99%.

TEST EXAMPLES

Test Example 1
Measurement of Inhibitory Activity on Angiotensin I Converting Enzyme The enzyme-decomposed materials from laver in Example 1 (1) & (2) were dissolved respectively at a predetermined concentration, and 50 μl aliquot was added to each test tube. Then, L-hippurylhistidyl leucine (Peptide Institute Inc.) as enzyme-substrate was dissolved at a concentration of 12.5 mM in a borate buffer (pH 8.3) containing 1.0 M sodium chloride, and 100 μl of this solution was added to each test tube and finally dissolved at 25 mU/ml in distilled water. 100 μl angiotensin I converting enzyme solution was added thereto and reacted at 37° C. for 1 hour. Thereafter, the reaction was terminated by adding 250 μl of 0.5 N HCl, and the reaction solution was left for 5 minutes. 1.5 ml of ethyl acetate was added thereto along the wall of the tube, stirred vigorously and centrifuged (3000 rpm, 10 minutes), and the upper layer (ethyl acetate layer), 0.5 ml, was collected. It was introduced into a drying oven, and the ethyl acetate was evaporated at 120° C. for 30 minutes, and the formed hippuric acid was dissolved in 3 ml of 1.0 M sodium chloride and its absorbance at 228 nm was measured.

The degree of inhibition is expressed in the following equation:

Degree of inhibition (%)={$(Ec-Es)/(Ec-Eb)$}×100 wherein Es is the absorbance of each sample, Ec is the absorbance of distilled water in place of the sample, and Eb is the absorbance of the same sample reacted after addition of the reaction terminating solution. The inhibitory activity $IC_{50}$ on angiotensin I converting enzyme is the concentration of a sample which is necessary for 50% inhibition of angiotensin I converting enzyme. The results are shown in Table 3.

TABLE 3

| Step | Inhibitory activity $IC_{50}$ for angiotensin I converting enzyme for each peptide mixture | Inhibitory activity $IC_{50}$ for angiotensin I converting enzyme for each protein |
|---|---|---|
| Dry laver → enzyme reaction | 1.52 | 0.53 |
| Dry laver → boiling treatment → enzyme reaction | 1.72 | 0.49 |
| Dry laver → boiling treatment → broth removal → enzyme reaction | 0.32 | 0.21 |
| Dry laver → boiling treatment → broth removal → enzyme reaction → secondary enzyme reaction | 1.85 | 0.42 |

As shown in Table 3, the enzyme-decomposed materials from laver obtained according to the process of the invention by boiling the dry laver and then removing the broth to raise the degree of decomposition with pepsin are estimated to contain a larger amount of formed peptides, and their inhibitory activity on angiotensin I converting enzyme is also strong. On the other hand, the enzyme-decomposed materials subjected to secondary enzyme reaction to confer good tastes thereon has a reduced inhibitory activity, but this activity is still at the same level as in the inhibitory activity of the product in the prior art (dry laver→enzyme reaction).

Test Example 2
Antihypertensive Effect By Administration Into Rats 15-week-old male spontaneous hypertensive rat (SHR) were purchased from Japan SLC, Inc. and preliminarily reared for 2 weeks, and 6 rats with a systolic blood pressure of 190 mmHg or more were used as one group, and 30 mg of the peptide mixture in Example 1 (1) (after subjected to boiling treatment) or of a comparative test sample not subjected to boiling treatment was orally administered. The systolic blood pressure in SHR tail arteries was determined 5 times for each measurement by a tail-cuff method before administration and 1, 2, 4, 6 and 8 hours after administration in an unbloody tail artery blood pressure measurement unit (MK-1030 model, Muromachi Kikai), and the highest and lowest blood pressures were rejected, and the average of the remaining 3 blood pressures was regarded as the blood pressure for each measurement. The results are shown in Table 4.

TABLE 4

|  | Pre | 1 hr | 2 hr | 4 hr | 6 hr | 8 hr |
|---|---|---|---|---|---|---|
| Example 1 | 204.3 ± 10.2 | 193.7 ± 29.3 | 190.1 ± 18.5 | 182.5 ± 12.2 | 186.2 ± 22.1 | 187.9 ± 15.2 |
| Dry laber → enzyme decomposition | 202.2 ± 8.7 | 193.7 ± 28.2 | 192.1 ± 27.4 | 191.7 ± 12.5 | 189.6 ± 13.5 | 194.8 ± 18.4 |

As shown in Table 4, the enzyme-decomposed materials produced in Example 1 (1) in the present invention possess a stronger antihypertensive action than that of the enzyme-decomposed materials produced by the process of dry laver→enzyme decomposition.

Test Example 3
Effect of Preventing High Blood Pressure and Cerebral Apoplexy By Long-term Administration Into Rats 5-week-old male spontaneous hypertensive rats liable to cerebral apoplexy were purchased from Charles River Japan, Inc., preliminarily reared and divided into the following 3 groups (7 animals per group): a group given commercial powder feed, a group given feed in which 0.5% enzyme-decomposed materials in Example 1 (1) were mixed with commercial powder feed, and a group given feed in which 1% enzyme-decomposed materials in Example 1 (1) were mixed with commercial powder feed, and the animals were allowed feed and drinking water (1% aqueous saline) ad libitum and examined for 2 months in a test by administration of mixed feed. The blood pressure was measured in an unbloody manner every week from the start of the test, and whether general symptoms and nerve symptoms occurred or not and whether the animals were alive or dead were examined once every day. The results are shown in FIG. 1 and Table 5.

TABLE 5

|  | Occurrence of cerebral apoplexy (%) | Number of survival days |
|---|---|---|
| Control group | 100 | 34 |
| 0.5% mixed feed group | 57 | 39 |
| 1% mixed feed group | 29 | 51 |

As shown in Table 5, it was confirmed that with an increasing content, in feed, of the enzyme-decomposed materials from laver according to the present invention, the degree of occurrence of cerebral apoplexy is decreased and the number of rat's survival days is prolonged. Further, as shown in FIG. 1, the systolic blood pressure was considerably lower in the group given 0.5% mixed feed and further lower in the group given 1% mixed feed than in the control group, and it was thus confirmed that the enzyme-decomposed materials from laver according to the present invention have the effect of preventing hypertension.

Test Example 4
Measurement of the Ability to Prevent Precipitation of Calcium

The ability to prevent precipitation of calcium as one mechanism of promotion of calcium absorption was judged by the ability to prevent precipitation of calcium chloride in the presence of the enzyme-decomposed materials in a phosphate buffer. That is, 3 ml of the purified enzyme-decomposed materials in Example 1 (3), dissolved at a predetermined concentration in distilled water, was mixed with 1 ml of 20 mM calcium chloride, and 4 ml of 5 mM phosphate buffer (pH=7.0) was added thereto, left at 37° C. for 2 hours, and centrifuged (3000xg, 10 minutes), and the calcium dissolved in the supernatant was measured. For comparison, the same experiment was conducted using casein phosphopeptide. Casein phosphopeptide has the effect of preventing precipitation of calcium and is widely used as food materials to facilitate absorption of calcium. The results are shown in FIG. 2.

Figure 2:
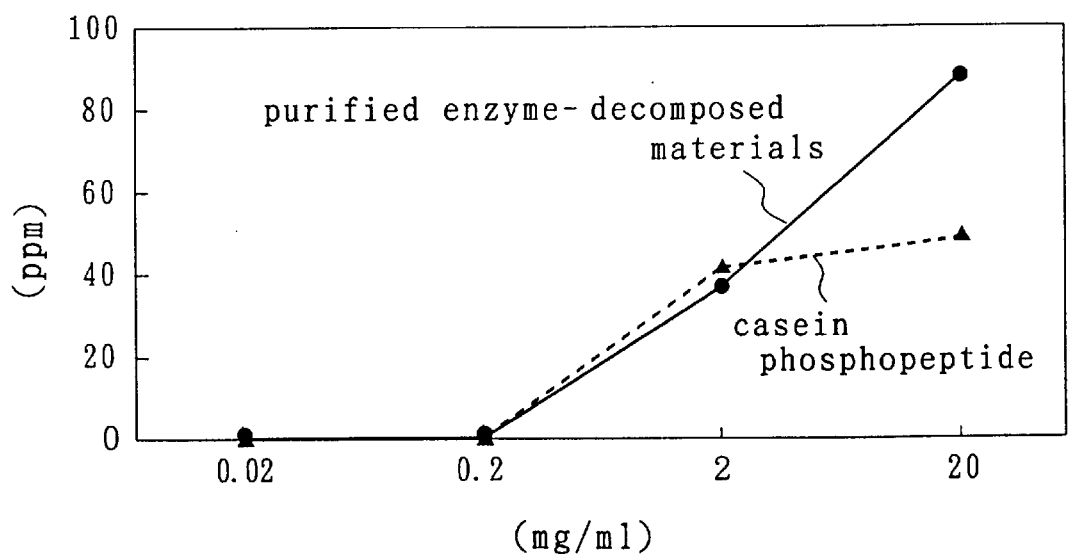
FIG. 2 is a diagram showing the result of a test for prevention of calcium precipitation by the enzyme-decomposed materials from laver according to the present invention.

In FIG. 2, the sample concentration (mg/ml) in distilled water was plotted on the abscissa and the calcium concentration (ppm) was plotted on the ordinate. As shown in FIG. 2, the effect of the purified enzyme-decomposed materials of the present invention preventing on precipitation of calcium is increased depending on the concentration, and their effect was confirmed to be almost equal to that of casein phosphopeptide.

Test Example 5
Measurement of Anti-mutagenic Activity

Anti-mutagenic activity as one of the effects of inactivating a carcinogen incorporated into the body was examined in an umu-test. The umu-test is one of mutagenicity tests where expression of an umu gene participating in mutation of *Salmonella typhimurium* bacteria is measured by using β-galactosidase activity as an indication. The mutagens Trp-P-1, AF-2 and IQ were added respectively to *Salmonella typhimurium* bacteria to cause mutation, and their β-galactosidase activity was measured by coloration of substrate X-gal, and the mutagenicity in this case was regarded as 100. Using this as a standard, the sample to which a predetermined amount of the enzyme-decomposed materials (subjected to secondary enzyme-decomposed materials) in Example 1 (2) was added was measured for β-galactosidase activity, and the degree of coloration of substrate X-gal was compared with the standard. The results are shown in FIG. 3.

Figure 3:
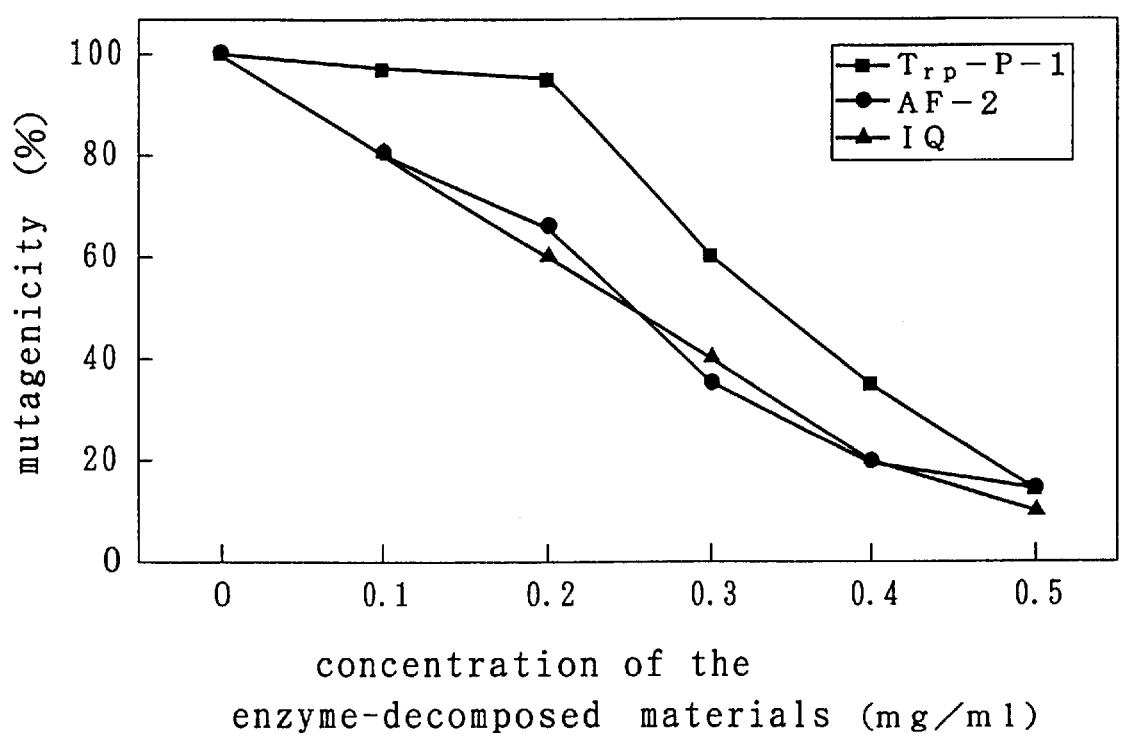
FIG. 3 is a diagram showing the result of a test for measuring the anti-mutagenic activity of the enzyme-decomposed materials from laver according to the present invention.

As shown in FIG. 3, as the concentration of the enzyme-decomposed materials in Example 1 (2) is increased, the antigenecity of any mutagens is reduced, and it was thus confirmed that the enzyme-decomposed materials have antigenic activity.

Test Example 6
The effect of Reducing Plasma Cholesterol Levels By Administration Into Rats As experimental animals, 4-week-old male Wistar strain ST rats were preliminarily reared on commercial solid feed for 1 week and then reared for 3 weeks where 5 animals were used as one group. The test feed was prepared by incorporating 1% (0.7% in terms of crude protein) of the enzyme-decomposed materials in Example 1 (1) into MF powder feed (Oriental Yeast Co., Ltd.), and the feed in the control group was MF powder feed. The feed was changed every day, and the animals were allowed the feed and drinking water ad libitum. The chamber used for rearing the animals was kept at room temperature (25° C.) under 50±5% humidity in the bright for 12 hours and in the dark for 12 hours (lighting at 8 A.M. and lighting-out at 8 P.M.). After the test, the rat heads were cut off, and blood was collected, and immediately lipid components (total cholesterol, free cholesterol, triglyceride and phospholipid) in plasma were quantified. The measurement results are shown in Table 6.

TABLE 6

|  | Control group | Test group |
|---|---|---|
| Total cholesterol (mg/dl) | 190 ± 6 | 122 ± 5 |
| Free cholesterol (mg/dl) | 40.8 ± 1.7 | 21.2 ± 1.3 |
| Triglyceride (mg/dl) | 63.2 ± 2.2 | 31.4 ± 1.4 |
| Phospholipid (mg/dl) | 177 ± 6 | 159 ± 3 |

As shown in Table 6, total cholesterol, free cholesterol, triglyceride and phospholipid in serum were reduced by administrating the enzyme-decomposed materials of the present invention, and the effect of improving lipid metabolism was thus confirmed.

Test Example 7

The effect of Reducing Lipid Levels in Plasma And Liver By Administration Into Mice As experimental animals, 4-week-old male ICR strain mice were preliminarily reared on commercial solid feed for 1 week and subjected to the test where 7 animals were used as one group. The test feed was prepared by incorporating 0.3% and 1% of the enzyme-decomposed materials in Example 1 (1) into MF powder feed supplemented with 0.5% cholesterol and 1% cholic acid, while the feed in the control group was MF powder feed supplemented with 0.5% cholesterol and 1% cholic acid. The chamber used for rearing the animals was kept at room temperature, 22±4° C., under 55±15% humidity in the bright for 12 hours and in the dark for 12 hours (lighting at 7 A.M. and lighting-out at 8 P.M.). After the 28-day test, blood was collected from the great veins in the abdomens under anesthesia with ether, and plasma lipid components (total cholesterol, HDL cholesterol and triglyceride) were quantified.

In the experiment for hepatic cholesterol, blood was collected from the above mice, then the livers were removed, weighed, and perfused with physiological saline, and a homogenate was prepared and measured for total cholesterol and triglyceride. LDL was determined by subtracting the HDL cholesterol level from the total cholesterol level.

The results are shown in Tables 7 and 8.

TABLE 7

| | Plasma | | | |
|---|---|---|---|---|
| | Total cholesterol | Triglyceride | HDL | LDL |
| Control group | 215.4 ± 1.6 | 71.2 ± 5.2 | 77.0 ± 4.2 | 138.7 ± 3.9 |
| 0.3% blend | 145.3 ± 3.0 | 50.0 ± 4.8 | 71.1 ± 6.8 | 74.2 ± 5.4 |
| 1.0% blend | 152.5 ± 3.3 | 49.0 ± 4.5 | 91.6 ± 5.5 | 60.9 ± 5.4 |

(mg/dl)

TABLE 8

| | Liver | |
|---|---|---|
| | Total cholesterol | Triglyceride |
| Control group | 6.8 ± 0.2 | 5.4 ± 0.6 |
| 0.3% blend | 7.0 ± 0.5 | 2.9 ± 0.3 |
| 1.0% blend | 7.7 ± 0.2 | 3.6 ± 0.2 |

(mg/g liver)

As shown in Tables 7 and 8, a reduction in plasma total cholesterol, triglyceride, LDL, and hepatic triglyceride was observed in the group given the enzyme-decomposed materials, as compared with the control group.

Test Example 8
Effect of Improving Hepatic Functions

As experimental animals, 6-week-old male Wister strain rats were preliminarily reared on commercial solid feed for 1 week and subjected to the test where 7 animals were used as one group. After preliminary rearing, the animals were reared for 14 days on standard feed (commercial powder feed), test feed I (prepared by incorporating 1% of the enzyme-decomposed materials in Example 1 (1) into the standard feed) and test feed II (prepared by incorporating 3% of the enzyme-decomposed materials into the standard feed). The chamber used for rearing the animals was kept at room temperature, 22±4° C., under 55±15% humidity in the bright for 12 hours and in the dark for 12 hours (lighting at 7 A.M. and lighting-out at 8 P.M.).

Then, a D-galactosamine hydrochloride (Sigma) solution (300 mg/ml) adjusted to pH 7.2 with 1 N sodium hydroxide was sterilized with a sterilization filter and injected intraperitoneally into the rats at a dose of 800 mg/kg on Day 14. The rats were starved for 4 hours before and after this administration, respectively. 20 hours after D-galactosamine was administered, the abdomens were opened under anesthesia with Nembutal, then blood was collected from the hearts, and plasma was separated and measured for transaminase activity.

Figure 4:
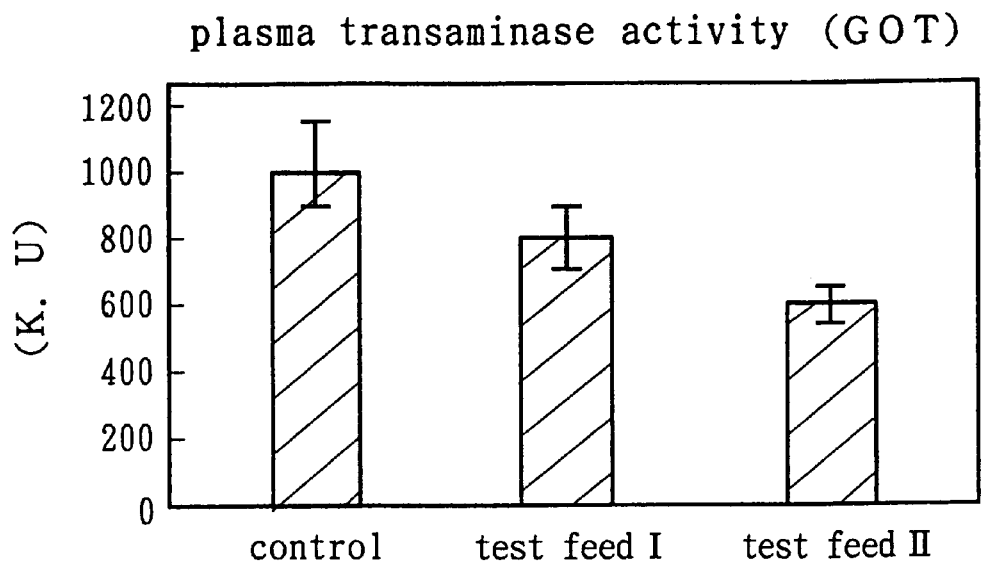
FIG. 4 is a diagram showing the result of a test for prevention of plasma transaminase activity (GOT) by the enzyme-decomposed materials from laver according to the present invention.
Figure 5:
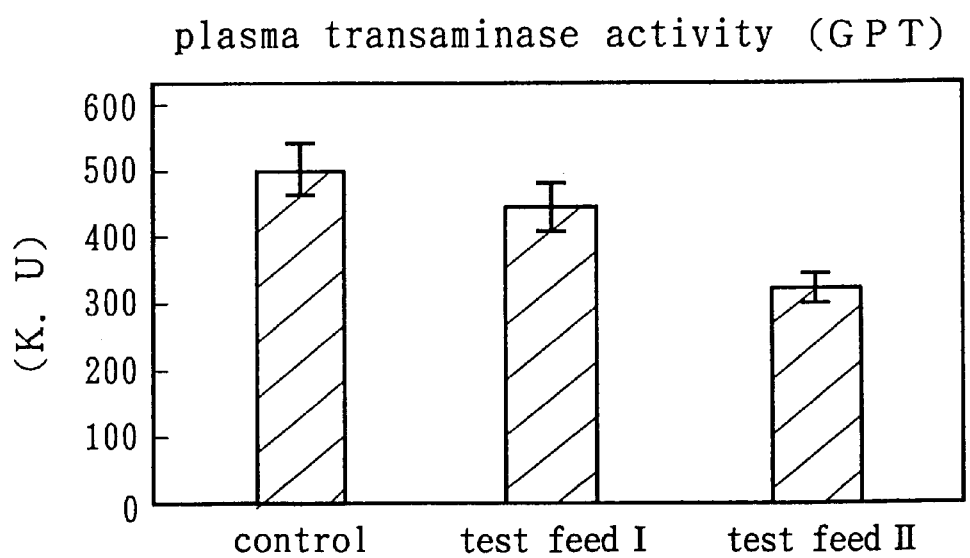
FIG. 5 is a diagram showing the result of a test for prevention of plasma transaminase activity (GPT) by the enzyme-decomposed materials from laver according to the present invention.

The results are shown in FIGS. 4 and 5. As shown in these figures, the group given the feed incorporating the enzyme-decomposed materials of the present invention indicated that the plasma transaminase (GOT, GPT) increase caused by galactosamine hepatic disturbance was inhibited in a concentration-dependent manner.

Test Example 9
Measurement of Superoxide Dismutase (SOD)-like Activity

The enzyme-decomposed materials in Example 1 (1) were fractionated into 4 fractions by application to Chromatorex-ODS DM 1020T (C18) and eluted with 0% aqueous ethanol. (fraction 1), 10% aqueous ethanol (fraction II), 20% aqueous ethanol (fraction III) and 50% aqueous ethanol (fraction IV) respectively in this order. The respective fractions were measured for SOD-like activity in the following manner. Three mM xanthine, 3 mM EDTA, 1 mM XTT (3'-1-[(phenylamino)-carbonyl]-3,4-tetrazolium}-bis(4-methoxy-6-nitro)benzenesulfonic acid hydrate), and 0.1 ml of 2% aqueous solution of each fraction was added to a test tube containing 2.5 ml of 50 mM sodium carbonate buffer (pH 10.2), and immediately 0.1 ml of 57 mU/ml XOD (xanthine oxidase) was added thereto. After each mixture was reacted at 25° C. for 20 minutes exactly, its absorbance at 470 nm was measured.

To correct the errors caused by direct involvement of the enzyme-decomposed materials in reducibility of XTT, the absorbance of a xanthine-free sample was also measured.

Using the absorbance of the xanthine-free sample as the control, the degree of inhibition was determined in the following equation:

Degree of inhibition (%)=control-(xanthine (+)-xanthine (-))/control×100

The concentration at which the reduction of XTT by $O_2^-$ was inhibited by 50% was defined to be 1 unit. The results are shown in Table 9.

TABLE 9

| Test solution | U/g |
|---|---|
| Fraction I | 1000 |
| Fraction II | 5000 |
| Fraction III | 20000 |
| Fraction IV | 50000 |

As shown in the table above, strong SOD-like activity was observed in fractions III and IV.

Test Example 10
Measurement of Anti-oxidant Action

The enzyme-decomposed materials in Example 1 (1) were fractionated into 4 fractions by application to Chromatorex-ODS DM 1020T (C18) and eluted with 0% aqueous ethanol (fraction 1), 10% aqueous ethanol (fraction II), 20% aqueous ethanol (fraction III) and 50% aqueous ethanol (fraction IV) respectively in this order. The respective fractions were measured for anti-oxidant activity in the following manner.

A mixture consisting of 51.5 mg linoleic acid, 4.052 ml ethanol, 4.0 ml of 0.05 M phosphate buffer (pH 7.0) and 1.948 ml of deionized water was used as the reaction solution, and 10 mg of each of the fractionated enzyme-decomposed materials was added to this mixture. This solution was sealed in a test tube equipped with a screw and left in a thermostatic chamber at 50° C., and the peroxide number of the linoleic acid was measured every 48 hours by the rhodan iron method. That is, 0.1 ml of the reaction solution, 9.7 ml of 75% ethanol, 0.1 ml of 30% rhodan ammonia, and 0.1 ml of 3.5% hydrochloric acid containing 0.02 M ferric chloride were added and reacted for 3 minutes, and its absorbance at 500 nm was measured. The number of days elapsed until the absorbance at 500 nm reached 0.35 was assumed to be induction period (days). As a result, the number of induction days suggesting the anti-oxidant action was 8 days for 3 mg α-tocopherol, whereas it was 7 days for fraction 1, 10 days for fraction II, 13 days for fraction III, and 15 days for fraction IV, and the anti-oxidant action was thus confirmed.

Test Example 11
Ability to Lower Blood Sugar Levels

Streptozotocin (STZ, Sigma) dissolved in 0.1 M citrate buffer (pH 4.5) was injected subcutaneously at 80 mg/kg into male Wister strain rats on Day 2 after birth to prepare STZ rats. Thereafter, the animals were breast-fed for 4 weeks and then reared on commercial solid feed for 4 weeks. According to blood sugar levels at the time of starvation, the animals were divided into groups each consisting of 7 animals, and the control group was given standard feed (commercial solid feed), and the test groups were given test feed I (prepared by incorporating 1% of the enzyme-decomposed materials in Example 1 (1) into the standard feed) and test feed II (prepared by incorporating 3% of the enzyme-decomposed materials into the standard feed), and the animals were reared for 8 weeks. The chamber used for rearing the animals was kept at room temperature, 22±2° C., under 55±10% humidity in the bright for 12 hours and in the dark for 12 hours (lighting at 7 A.M. and lighting-out at 8 P.M.). After the experiment was initiated, blood was collected via tail veins after 5 hours of starvation at 2-week intervals to measure glucose levels in plasma.

Figure 6:
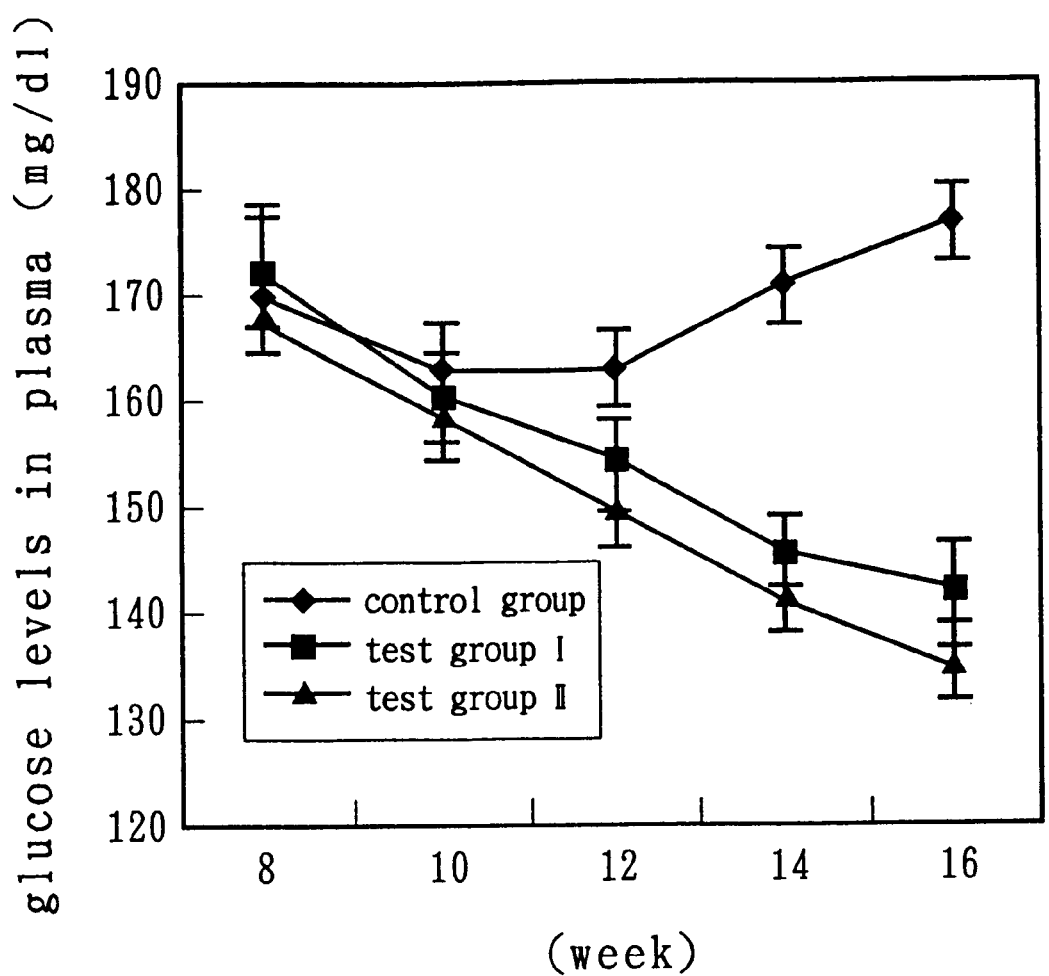
FIG. 6 is a diagram showing the result of a test for reduction of blood sugar levels by the enzyme-decomposed materials from laver according to the present invention.

The results are shown in FIG. 6. As shown in FIG. 6, the group given the feed incorporating the enzyme-decomposed materials of the present invention, as compared with the control group, showed a reduction in the glucose levels in plasma in a concentration-dependent manner.

EXAMPLE 2

The enzyme-decomposed materials from laver prepared in Example 1 (1) were dissolved at 5% by weight in chicken eggs to prepare 50 g beaten eggs which were then combined with a soup stock prepared from 6 g common salt, 3 g soy sauce, 3 g granulated sugar, 2 g of flavor seasoning (bonito, shii-take mushroom, sea tangle) and 150 g water, and the resulting soup was placed on a tray (50 g soup/tray) and lyophilized to prepare an instant egg soup.

EXAMPLE 3

8% by weight of the enzyme-decomposed materials from laver prepared in Example 1 (1), 45% by weight of soy sauce with a salt content reduced by 40%, 10% by weight of EDM, 5% by weight of a bonito extract, 2% by weight of a yeast extract, 0.01% by weight of a cayenne pepper extract and 30% by weight of water were mixed and heated to prepare a flavoring solution of seasoned laver. 1 ml of this solution was applied onto both faces of toasted laver and dried to prepare seasoned laver. It was seasoned laver with a 30% lower salt content than a conventional product of our company with no sodium glutamine added.

EXAMPLE 4

2% by weight of the enzyme-decomposed materials from laver prepared in Example 1 (2), 17% by weight of soy sauce with a salt content reduced by 40%, 17% by weight of sweet sake, 34% by weight of a bonito extract, 2% by weight of sugar and 28% by weight of water were mixed and heated to prepare a low-salt sauce for noodles.

EXAMPLE 5

80% by weight of the enzyme-decomposed materials from laver prepared in Example 1 (1) and 20% by weight of lactose were mixed and tabletted in a tabletting machine to prepare tablets having an antihypertensive action.

EXAMPLE 6

1% by weight of the enzyme-decomposed materials from laver prepared in Example 1 (2), 9% by weight of soluble soy protein, 15% by weight of sugar, 1% by weight of conc. lemon juice, 0.2% by weight of thickening polysaccharide, 0.1% by weight of yogurt flavor and 73.7% by weight of water were mixed, bottled and sterilized to prepare a protein drink with a protein score of 98.

EXAMPLE 7

5 g of the purified enzyme-decomposed materials from laver prepared in Example 1 (3), 9 g sodium chloride, 5 g chlorobutanol and 1 g sodium hydrogen carbonate were dissolved in 1000 ml distilled water and introduced into 2 bottles for drip infusion, to prepare an antihypertensive intravenous infusion.

According to the present invention, laver is previously subjected to boiling treatment and broth-removing treatment before pepsin decomposition, whereby enzyme-decomposed materials having a high antihypertensive action, an inhibitory action on calcium precipitation, an anti-oxidant effect, a SOD-like activity, plasma and hepatic cholesterol-reducing action, an effect of reducing blood sugar levels and an effect of improving hepatic functions can be obtained to provide an useful antihypertensive agent having no side effects as described above. Further, the enzyme-decomposed materials are previously subjected to boiling treatment and broth-removing treatment before pepsin decomposition, whereby their bitter taste and unfavorable smell are removed and their viscosity is lowered, so these materials become further useful as ingredients in health food. In particular, if these materials are subjected to secondary decomposition with an enzyme having a peptidase activity, they becomes also excellent in tastes. Accordingly, the materials can also be used not only ingredients in health food but also as seasonings.

What is claim:

1. An enzyme-decomposed material from laver, comprising a peptide mixture obtained by boiling laver as a starting material in water for 1 hour or more to form a broth, then removing the broth and adding water and pepsin to the remaining laver to decompose the laver with pepsin.

2. An antihypertensive composition comprising the enzyme-decomposed material from laver according to claim 1 as an active ingredient.

3. A low salt health food comprising the enzyme-decomposed material of claim 1 and a low salt food, whereby said enzyme-decomposed material is added to the low salt food in therapeutically effective amounts.

4. A health food comprising the enzyme-decomposed material of claim 1 and a food, whereby said enzyme-decomposed material is added to the food in therapeutically effective amounts.

5. Health food according to claim 4, which has the effect of preventing precipitation of calcium.

6. Health food according to claim 4, which has an anti-mutagenic activity.

7. Health food according to claim 4, which has the effect of reducing plasma cholesterol.

8. Health food according to claim 4, which has the effect of preventing cerebral apoplexy.

9. Health food according to claim 4, which has the effect of reducing hepatic cholesterol.

10. Health food according to claim 4, which has the effect of improving hepatic functions.

11. Health food according to claim 4, which has a SOD-like activity.

12. Health food according to claim 4, which has an anti-oxidant effect.

13. Health food according to claim 4, which has the effect of reducing blood sugar levels.

14. An enzyme-decomposed material from laver comprising a peptide mixture obtained by boiling laver as a starting material in water for 1 hour or more to form a broth, then removing the broth, adding water and pepsin to decompose the laver with pepsin, and further decomposing said laver with an enzyme having a peptidase activity.

15. The enzyme-decomposed material from laver according to claim 14 wherein free amino acid levels are 10% or more.

16. An antihypertensive agent comprising the enzyme-decomposed material from laver according to claim 14 as an active ingredient.

17. A seasoning comprising the enzyme-decomposed material from laver described in claim 14 as a major ingredient.

18. A health food comprising the enzyme-decomposed material of claim 14 and a food, whereby said enzyme-decomposed material is added to the food in therapeutically effective amounts.

19. A low salt health food comprising the enzyme-decomposed material of claim 14 and a low salt food, whereby said enzyme-decomposed material is added to the low salt food in therapeutically effective amounts.

20. A method of forming an enzyme-decomposed material comprising a peptide mixture, said method comprising boiling laver as a starting material in water for 1 hour or more to form a broth, then removing the broth and adding water and pepsin to the remaining laver to decompose the laver with pepsin and obtain the enzyme-decomposed material comprising the peptide mixture.

* * * * *